United States Patent
Singh et al.

(10) Patent No.: US 7,955,738 B2
(45) Date of Patent: *Jun. 7, 2011

(54) POLYMER IONIC ELECTROLYTES

(75) Inventors: Rajiv R. Singh, Getzville, NY (US); Martin R Paonessa, Niagara Falls, NY (US); Ian R Shankland, Randolph, NJ (US)

(73) Assignee: Honeywell International, Inc., Morristown, NJ (US)

( * ) Notice: Subject to any disclaimer, the term of this patent is extended or adjusted under 35 U.S.C. 154(b) by 1339 days.

This patent is subject to a terminal disclaimer.

(21) Appl. No.: 11/072,915

(22) Filed: Mar. 4, 2005

(65) Prior Publication Data

US 2005/0196676 A1 Sep. 8, 2005

Related U.S. Application Data

(60) Provisional application No. 60/550,471, filed on Mar. 5, 2004.

(51) Int. Cl.
 *H01M 6/14* (2006.01)
 *H01M 6/04* (2006.01)

(52) U.S. Cl. .......... 429/303; 429/33; 429/200; 429/336; 429/339; 361/526; 252/62.2; 216/99; 136/252

(58) Field of Classification Search ... 546/1; 548/300.1; 429/303, 200, 33, 336, 339, 229, 206; 361/526; 361/252; 252/62.2; 216/99; 534/15; 136/252
See application file for complete search history.

(56) References Cited

U.S. PATENT DOCUMENTS

| 5,073,674 A | 12/1991 | Olah | 585/725 |
|---|---|---|---|
| 5,763,728 A * | 6/1998 | Kocal et al. | 585/724 |
| 5,965,054 A | 10/1999 | McEwen et al. | 252/62.2 |
| 6,096,922 A * | 8/2000 | Lal | 562/822 |
| 2002/0041860 A1* | 4/2002 | Requejo | 424/76.1 |

FOREIGN PATENT DOCUMENTS

| EP | 1 235 294 | | 8/2002 |
|---|---|---|---|
| EP | 1 515 346 | | 3/2005 |
| JP | 57-92502 | * | 6/1982 |
| JP | 57-092502 | | 6/1982 |
| WO | 02/060838 | | 8/2002 |
| WO | 2004/059664 | | 7/2004 |
| WO | WO2005007675 | | 1/2005 |
| WO | WO2005092859 | | 10/2005 |

OTHER PUBLICATIONS

Rika Hagiwara, Takayuki Hirashige, Tetsuya Tsuda, and Yasuhiko Ito, A Highly Conductive Room Temperature Molten Fluoride:EMIF2.3HF, Journal of the Electrochemical Society, 149 (1) D1-D6 (2002). The Electrochemical Society, Inc.*

Material Safety Data Sheet, Pyridine 3HF Ionic Liquid from Honeywell, Current Issue Date: Apr. 2003, http://www.honeywell.com/sites/docs/DOBL7UN38PJ0LJ5PYTE4IP69K7MBZT61O.pdf.*

Hagiwara et al., "Acidic 1-ethyl-3-methylimidazolium flouride: a new room temperature ionic liquid," *Journal of Flourine Chemistry*, 99, 1-3(1999).

Hagiwara et al., "A Highly Conductive Room Temperature Molten Flouride: EMIF-2.3 HF," *Journal of Electrochemical Society*, 149(1), D1-D6(2002).

Welton, "Room-Temperature Ionic Liquids. Solvents for synthesis and catalysis," *Chem. Rev.*, 99, 2071-2083(1999).

Hong et al., "Conventional free radical polymerization in room temperature ionic liquids: A Green Approach to Commodity Polymers with practical Advantages," *Chem. Comm.*, 1368-1369(2002).

Scott et al., Application of ionic liquids as plasticizers for poly(methyl methacrylate), *Chem. Comm*, 1370-1371(2002).

Klilngshirn et al., "Polar, non-coordinating ionic liquids as solvents for the alternating copolymerization of styrene and CO catalyzed by cationic palladium catalysts," *Chem. Comm.*, 1394-1395(2002).

Swatloski et al. "Dissolution of cellose [(sic.)] with Ionic Liquids," *J. Am. Chem. Soc.*, 124, 4974-4975(2002).

Sheldon et al., "Biocatalysis in ionic liquids," *Green Chem.*, 4,147-151(2002).

Sheldon, "Catalytic reactions in Ionic liquids,"*Chem. Comm.*,2399-2407(2001).

Huddleston et al., "Characterization and comparison of hydrophilic and hydrophobic room temperature ionic liquids incorporating the imidazolium cation," *Green Chem.*, 3, 156-164(2001).

Holbrey et al., "Ionic Liquids (rev.)," *Clean Products and Proc.* , 1, 223-236(1999).

Gordon, "New Developments in Catalysis using ionic liquids," *Applied Catalysis A: General*, 222,101-117(2001).

Wasserscheid et al., "Ionic Liquids—New "Solutions" for Transition Metal Catalysis," *Angew. Chem. Int. Ed.*, 39, 3772-3789(2000).

T Tsuda, et al; A Hghly Conductive Composite of Electrolyte Consisting of Polymer and Room Temperature Molten Fluorohydrogenates; Solid Stat Ionics, North Holland Pub. Company, Amsterdam, NL; vol. 149: No. 3-4; Aug. 2, 2002; pp. 295-298; XP004370988.

* cited by examiner

*Primary Examiner* — Ling-Siu Choi
*Assistant Examiner* — Bijan Ahvazi

(57) ABSTRACT

Polymeric ionic gels of ionic liquids having melting points below about 100° C. that are formed by the reaction of a heterocyclic amine with about 2.8 and about 3.2 moles of anhydrous hydrogen fluoride per mole of amine nitrogen. Electrochemical devices having non-aqueous electrolytes containing the ionic liquids and polymeric ionic gels are also disclosed.

10 Claims, No Drawings

POLYMER IONIC ELECTROLYTES

CROSS REFERENCE TO RELATED APPLICATION

The present application claims priority benefit under 35 U.S.C. §119(e) of U.S. Provisional Application No. 60/550,471 filed Mar. 5, 2004, the disclosure of which is incorporated herein by reference.

BACKGROUND OF THE INVENTION

The present invention relates to ionic liquids and methods for their preparation. In particular, the present invention relates to ionic liquids that are liquid at relatively low temperatures. Ionic liquid compounds according to the present invention are liquid at temperatures below about 100° C., and are preferably liquid below about 60° C., and more preferably are liquid at or near ambient temperature. The present invention further relates to polymeric ionic electrolytes and methods for their preparation. In particular, the present invention relates to gelling the ionic liquids of the present invention by adding certain polymers. Polymeric compounds according to the present invention are gel-like at temperatures between about 0° and about 200° C., and have conductivities of greater than 5 millisiemens/cm at or near ambient temperature.

There is currently great interest in the use of ionic liquids as solvents for a wide range of applications. Ionic liquids are low melting point salts that, being composed entirely of ions, posses negligible vapor pressures. By carefully choosing among a wide range of possible cations and anions, ionic liquids may be prepared that are liquid at low temperatures. A number of other solvent properties can be controlled as well, such as polarity and other factors that determine a liquid's suitability as a solvent for a given end-use application.

Conventional organic solvents are high on the list of hazardous chemicals because they are typically volatile liquids that are used in large quantity and produce harmful vapors that are difficult to contain. Ionic liquids, on the other hand, are non-volatile, non-flammable and highly stable solvents, and as such are rapidly emerging as promising replacements for the traditional volatile organic solvents.

Not only do ionic liquids have utility as industrial solvents, they are also suitable, for example, as highly polar solvents for use in preparative chemistry, and as catalysts. The negligible vapor pressure of ionic liquids facilitates product separation by fractional distillation. They also have particular application in electrochemistry, for example, in batteries, fuel cells, and photovoltaic devices and in electrodeposition processes.

International Application No. PCT/GB00/01090 discloses ionic liquids that are specific quaternary ammonium salts of zinc, tin and iron halides. The disclosed ionic liquids are reportedly liquid below 60° C. and inexpensive to produce. The quaternary ammonium salts of zinc and tin, and iron halides, are reportedly less water sensitive that earlier prior art ionic liquids, which were quaternary ammonium salts of aluminum trichloride.

Hagiwara et al., *J. Fluorine Chem.* 99, 1 (1999), and *J. Electrochem. Soc.*, 149, D1 (2002), have recently disclosed several ionic liquids comprising various imidazolium fluorides combined with hydrogen fluoride at a specific mole ratio of 1:2.3. Otherwise, prior art salts are minimally electrically conductive, and all are viscous liquids. There remains a need for ionic liquids with greater fluidity for solvent applications and with an electrical conductivity better suited for electrochemical applications.

There is also currently great interest in the use of polymeric gels as electrolytes for a wide range of applications. Polymeric gels are low volatility, highly viscous materials that, being composed almost entirely of polymers, posses negligible vapor pressures.

Conventional electrolytes are high on the list of hazardous chemicals because they are typically volatile liquids that are used in large quantity and produce harmful spills that are difficult to contain in consumer applications. Ionic gels, on the other hand, are non-volatile, non-flammable and highly stable materials, and as such are rapidly emerging as promising replacements for the traditional liquid electrolytes. They also have particular application in electrochemistry, for example, in super capacitors, batteries, fuel cells, and photovoltaic devices and in electrodeposition processes.

Yoshida et al., *Sci. Tech. J.*, 38, 39-45 (June 2002) disclosed polymeric electrolyte gels formed by adding cellulosic materials and a cross-linking reagent to an electrolyte solution of $LiBF_4$ in a mixture of ethylene carbonate and diethyl carbonate. The disclosure shows that the conductivities of these gels are less than 3 milli-siemens/cm. There is thus also a need for polymeric gels with higher electrical conductivities.

SUMMARY OF THE INVENTION

These needs are met by the present invention. It has now been discovered that ionic liquids that are formed from heterocyclic amines using approximately three moles of hydrogen fluoride per amine nitrogen are orders of magnitude more electrically conductive than the quaternary ammonium salts of zinc, tin and iron halides. More specifically, it has been discovered that when heterocyclic amines are mixed with between about 2.8 and 3.2 moles of hydrogen fluoride per mole of amine nitrogen, but an ionic liquid is obtained having desirable salt-like properties that will form a highly conductive polymeric gel.

Therefore, according to one aspect of the present invention, ionic liquids are provided having melting points below about 100° C., formed by the reaction of a heterocyclic amine with between about 2.8 and about 3.2 moles of anhydrous hydrogen fluoride per mole of amine nitrogen, to which are added an amount of a polyacrylic acid or a Group I metal salt thereof effective to gel the ionic liquid.

Ionic liquids suitable for use with the present invention may consist of a salt of a single heterocyclic amine according to the present invention, or of two or more heterocyclic amines. A single heterocyclic compound may contain a plurality of amine nitrogen atoms, each of which is converted to a salt.

Mixing the ionic liquids of the present invention with polyacrylic acids or the Group I metal salts thereof produces polymeric ionic gels that are orders of magnitude more electrically conductive than the polymeric electrolyte gels disclosed Yoshida et al. More specifically, when the ionic liquids of the present invention are combined with an amount of a polyacrylic acid or its salts effective to gel the ionic liquid, not only are the prior art shortcomings resolved, a polymeric ionic gel is also obtained having a desirable gel-like rheology. The ionic liquids of the present invention also desirably have a very high electrical conductivity. Preferred polymeric ionic gels according to the present invention contain from about 2 to about 50% by weight of polymer.

For purposes of the present invention, polyacrylic acids are defined as including copolymers of acrylic acid with other vinyl monomers, including acrylic acid alkyl esters such as methyl acrylate, ethyl acrylate, and the like; alkyl-branched acrylic acids such as methacrylic acid, and esters thereof, such as methyl methacrylate, ethyl methacrylate, and the like; vinyl halides, such vinyl chloride, vinylidene chloride, and the like; and other vinyl monomers, such as vinyl acetate, vinyl alcohol, vinyl ethers, maleic anhydride, acrylonitrile, styrene, and the like. Polyacrylic acids are defined as including acrylic acid copolymerized with two or more of the foregoing. Suitable Group I metal salts according to the present invention include lithium, sodium and potassium.

The polymeric ionic gels of the present invention are also particularly well suited for use as non-aqueous electrolytes in electrochemical devices such as electrochemical capacitors, photovoltaic devices, potentiometric and voltametric electrochemical sensors, batteries, fuel cells and electrodeposition devices. The present invention therefore includes such electrochemical devices in which a positive electrode and a negative electrode are in conductive contact with a non-aqueous electrolyte gel essentially consisting of a polymer ionic gel according to the present invention as the non-aqueous electrolyte.

DETAILED DESCRIPTION OF PREFERRED EMBODIMENTS

Ionic liquids of the present invention, which function as ionic liquids singularly or when two or more are mixed together, are prepared by forming a salt of a heterocyclic amine with hydrogen fluoride. Heterocyclic amines suitable for use with the present invention may be aromatic such as pyrrole, imidazole, purine, pyrazole, pyridine, pyridazine, pyrazine, quinoline, quinazoline, pyrimidine, and the like, or they may be non-aromatic, such as pyrrolidine, pyrrolidone, piperazine, piperidine and the like, which are fully saturated, and pyrroline, and the like, which is non-aromatic, but unsaturated.

Heterocyclic amines suitable for use with the present invention includes single-ring compounds containing from five to seven ring members, with from one to three ring members being a heteroatom, at least one of which is nitrogen. Other suitable heteroatom ring members include oxygen, sulfur, and the like. Single-ring heterocyclic amines containing from one to three nitrogen atoms are preferred, with structures in which all ring heteroatoms are nitrogen atoms being more preferred.

Heterocyclic amines suitable for use with the present invention also include multi-cyclic fused two or three ring structures with from eight to fourteen ring members containing from one to three heteroatoms, at least one of which is nitrogen. Multi-cyclic two ring fused structures containing from eight to ten ring members are preferred. Again, the ring structure may include other heteroatoms such as oxygen, sulfur), and the like. Multi-cyclic fused ring structures containing from one to three nitrogen atoms are preferred, with structures in which all ring heteroatoms are nitrogen being the most preferred.

Heterocyclic amines suitable for use with the present invention include dimers and trimers of the same or different single-ring or multi-cyclic fused-ring structure directly bonded together, such as bis-pyridine. Dimers are preferred. Instead of being directly linked together, the ring structures of dimers and trimers may be linked by appropriate bi-functional ligands.

Heterocyclic amines suitable for use with the present invention may also be ring-substituted. A single ring substituent may be present, or up to three of the same or different substituents may be employed. The ring-substituents may be attached to a carbon atom or a suitable nitrogen atom.

Examples of suitable ring-substituents include, but are not limited to, halogen (including chlorine, bromine, fluorine and iodine), amino, cyano, hydroxyl, nitro, keto, phenyl, one to three carbon atom lower alkyl, two to four carbon atom alkene or alkyne, three to six carbon atom cycloalkyl or cycloalkene, one to four carbon atom aldehyde, $-R_1C(=O)R_2$, $-R_1OR_2$, $-R_1OC(=O)R_2$, $-R_1C(=O)OR_2$, and the like, wherein $R_1$ is a bond, a one to three carbon atom lower alkyl, a two to three carbon atom alkene, or phenyl, and $R_2$ is hydrogen, a one to three carbon atom lower alkyl, a two to three carbon atom alkene or phenyl. The $R_1$ and $R_2$ lower alkyl, alkene and phenyl groups may be further optionally substituted with one or more halogen, amino, cyano, hydroxyl, nitro, phenyl, one to three carbon atom lower alkyl and one to three carbon atom lower alkoxy. The preferred substituent groups include $C_aH_bBr_cCl_dF_eI_fN_gO_h$, where a is between 1 and 3, b, e are between 0 and 9, c, d, f, g and h are each between 0 and 2, and the sum of b through h is between 1 and 9, inclusive. When more than one substituent group is present, the substituents may be the same or different.

Heterocyclic amine salts according to the present invention have a melting point below about 100° C. For purposes of the present invention, "melting point" is determined by Differential Scanning Calorimetry. Among the heterocyclic amine salts of the present invention, those having a melting point less than about 60° C. are preferred, with heterocyclic amine salts having a melting point below room temperature being even more preferred. For purposes of the present invention, room temperature is defined as 25° C. The heterocyclic amine salts according to the present invention also have a viscosity between about 1 and about 100,000 centipoise when measured at room temperature using a vibrating reed viscometer. A viscosity less than 10,000 centipoise is preferred.

Ionic liquids according to the present invention have a specific conductivity between about one and about 600 milli-siemens/cm (mS/cm) and preferably greater than about 20 milli-siemens/cm, as measured by a common conductivity meter suitable for measuring conductivity in corrosive atmospheres such as in hydrogen fluoride.

Examples of specific heterocyclic amine compounds within the scope of the present invention include pyridine and substituted pyridine compounds such as α-picoline (2-methyl-pyridine), 2-amino-3-methylpyridine, niacin, niacinamide (Vitamin B), 2-aminopyridine, β-picoline (3-methylpyridine), 3-cyanopyridine, 4-cyanopyridine, 4-dimethylaminopyridine, 1,3-di-(4-pyradyl)-propane, 4-ethylpyridine, γ-picoline (4-methylpyridine), 2,6-lutidine, 3,5-lutidine, mixed picolines, mixed alkyl pyridines, 4-phenylpropylpyridine, polyalkylpyridine, pyridoxine (Vitamin $B_6$), 3-pyridylcarbinol, 2-vinylpyridine, 4-vinylpyridine, and the like.

Examples of non-pyridine heterocyclic amines also suitable for use with the present invention include piperidine and substituted piperidine compounds such as 2-ethanol-piperidine, 1,3-di-(4-piperidinyl)propane, and the like; pyrrole and substituted pyrroles; pyrrolidine and substitutes pyrrolidines; pyrrolidone and substitutes pyrrolidones such as N-methylpyrrolidone; imidazolines and substituted imidazolines; oxazole and substituted oxazoles; thiazole and substituted thiazoles; pyrazole and substituted pyrazoles; pyrroline and substitutes pyrrolines; pyrimidine and substitutes pyrimidines; purine and substitutes purines; quinoline and isoquinoline and substituted quinolines and isoquinolines; and the like.

Ionic liquids according to the present invention may be prepared simply by mixing together one or more heterocyclic amines with a stoichiometric amount of anhydrous hydrogen fluoride, i.e., between about 2.8 and about 3.2 moles of anhydrous hydrogen fluoride per mole of amine nitrogen, in a metal or plastic sealed vessel with an agitator, such as an Autoclave, with a sealed connection to the anhydrous HF supply, typically another sealed vessel. The vessel should be jacketed to remove heat inasmuch as the salt formation is highly exothermic. The vessels and the connection therebetween are sealed to protect against environmental exposure to anhydrous HF. The anhydrous HF may also be delivered in the form of Olah's reagent, the preparation of which is disclosed in U.S. Pat. No. 5,073,674.

No additional solvent is generally employed, although it may be advantageous in some circumstances to carry out a reaction in a solvent that is an ionic liquid, in particular, an ionic liquid according to the present invention. Excess reagents are readily removed by distillation because of the negligible vapor pressure of the salt product.

Optional solvents may then be used that are not ionic liquids to dissolve and further dilute the viscosity of the ionic liquids of the present invention, for example for use in electrochemical applications such as fuel cells, electrochemical capacitors, non-aqueous rechargeable batteries such as lithium batteries, photovoltaic cells and the like. The solvents are preferably polar in nature and include common solvents such as propylene carbonate, acetonitrile, and the like.

Ionic liquids according to the present invention include mixtures of two or more ionic liquid compounds according to the present invention. Such ionic liquids may be prepared by starting with a corresponding mixture of heterocyclic amines, or each ionic liquid compound may be individually prepared and then combined to form an ionic liquid mixture.

Polymeric ionic gels according to the present invention are prepared by adding an effective amount of one or more polyacrylic acids or salts thereof to the ionic liquids of the present invention with mixing until a uniform, homogenous gel is formed. The mixing is performed at a temperature at which the mixture is sufficiently fluid to permit thorough mixing, typically between about 0° C., and about 60° C., and preferably at ambient temperature, depending upon the choice of ionic liquid and polymers. Preferred methods simply add the polymer as an additional process step of the ionic liquid manufacturing process, more preferably before the exothermic heat of ionic liquid formation has been dissipated, so that an external source of heat is not needed to form the gel.

An amount of polymer between about 2 to about 50% by weight is preferred, with an amount between about 5 and 20% by weight being more preferred. Polyacrylic acids suitable for use with the present invention have a weight-average molecular weight between about 1000 and about 500,000. Group I metal salts, such as lithium, sodium and potassium polyacrylates can be used, as well as vinyl copolymers of the above-listed acrylic acids and acrylic acid salts, i.e., acrylic acid alkyl esters, alkyl-branched acrylic acids and esters thereof, vinyl halides, vinyl acetate, vinyl alcohol, vinyl ethers, maleic anhydride, acrylonitrile, styrene, combinations thereof, and the like.

Polymeric ionic gels according to the present invention have a melting point below about 150° C., measured by Differential Scanning Calorimetry. Among the polymeric ionic gels of the present invention, those having a melting point less than about 100° C. are preferred.

The polymeric ionic gels according to the present invention have a viscosity greater than about 10 centipoise when measured at 20° C. using a vibrating reed viscometer. A viscosity greater than about 100 centipoise at 20° C. is preferred, with a viscosity greater than about 500 centipoise at 20° C. being even more preferred. As with the ionic liquids of the present invention, optional solvents may be used that are not ionic liquids to dissolve and further dilute the viscosity of the polymer ionic gels of the present invention. The polymeric ionic gels to which the solvents are added may be based on solvent-free ionic liquids according to the present invention, or ionic liquids according to the present invention that contain the same or a different solvent.

The difference in conductivity between the ionic liquids according to the present invention and the polymeric ionic gels prepared therefrom is minimal, so that polymeric ionic gels according to the present invention have a specific conductivity between about one and about 600 milli-siemens/cm (mS/cm) and preferably greater than about 20 milli-siemens/cm, as measured by a common conductivity meter suitable for measuring conductivity in corrosive atmospheres.

The ionic liquids according to the present invention may be used for a wide range of purposes; for example, the liquids are useful for carrying out applications such as chemical reactions in preparative chemistry where a polar but non-aqueous solvent or a solvent with negligible vapor pressure is required. The ionic liquids according to the present invention may also be employed as thermal storage fluids. They may further be employed as inert media, for example, for dissolving ionic species such as transition metal complexes, and, either alone, or after complexing with other metal ions, as catalysts, or as chemical reagents.

Solvent system applications wherein a polar but non-aqueous solvent is required for which the ionic liquids of the present invention are useful include cellulose recycling, catalytic cracking reactions such as polyethylene recycling, chiral catalysis, coupling reactions, such as the Heck reaction, sulfonation reactions, nitration reactions, oxidation reactions, nucleophilic substitution reactions, olefin polymerization reactions, actinide extractions, alkylation reactions, hydroformylation reactions, dimerization reactions, hydrogenation reactions, Diels-Alder reactions, metathesis reactions, arylation reactions, Friedel—Crafts reactions, and the like.

The ionic liquids and polymeric ionic gels of the present invention are particularly well suited as non-aqueous electrolytes in electrochemical devices such as electrochemical capacitors, photovoltaic devices, potentiometric and voltametric electrochemical sensors, batteries, fuel cells and electrodeposition devices. The present invention therefore includes such electrochemical devices in which a positive electrode and a negative electrode are in conductive contact with a non-aqueous electrolyte essentially consisting of an ionic liquid of the present invention or a polymeric ionic gel prepared therefrom. Other conventional electrolyte additives may be present. The devices are otherwise essentially conventional and require no further description. One having ordinary skill in the art will understand how to use ionic liquids according to the present invention as a non-aqueous electrolyte for such devices. Polymeric ionic gels according to the present invention may also be used as thermal storage fluids.

EXAMPLES

A few of a number of preferred embodiments of the invention are illustrated in the following non-limiting examples.

Example 1

Formation of Pyridine Salt with Hydrogen Fluoride

About 60 grams of anhydrous hydrogen fluoride was added slowly to about 55 grams of pyridine contained in an autoclave with stirring, giving a pyridine to HF mole ratio of 1:3.

When the heat of the reaction subsided and the mixture cooled down, the autoclave contained 115 grams of a liquid, boiling at 180° C., 90° C. higher than that of pyridine and 160° C. higher than that of hydrogen fluoride. The liquid could not be separated into the constituents. The analysis of the material confirmed the structure of the new compound as the ionic liquid [pyridine H$^+$][H$_2$F$_3$]$^-$ (or pyridine·3HF). The conductivity of the pure ionic liquid was measured as 98 mS/cm. The liquid did not etch borosilicate glass, unlike Olah's reagent, which reacts with glass.

The ionic liquid was dissolved in propylene carbonate, where it was soluble in all proportions, and the conductivity was measured. The conductivity smoothly varied from 0 to 98 mS/cm as a function of the ionic liquid concentration.

The ionic liquid of was also dissolved in acetonitrile, where it again was soluble in all proportions, and the conductivity measured. The conductivity smoothly varied again, with a maximum at 104 mS/cm at about 80 wt % ionic liquid concentration.

Example 2

Gellation of HF Pyridine Salt

Example 1 was repeated, but before removing the ionic liquid from the autoclave, sodium polyacrylate (mol wt 50,000) was added with stirring. The solution became viscous and at 15 wt % sodium polyacrylate the liquid gel became too viscous to stir. The conductivity was measured, and was still 78 mS/cm. Conductivity measurements were made with increasing polymer content, and smoothly varied from 78 to 98 mS/cm as a function of the polymer concentration.

Example 3

Formation of Gel with Potassium Polyacrylate

Example 2 was repeated with potassium polyacrylate as the polymer. The results were the same, with a noticeable increase in the rate of formation of the gel. The gel conductivity at 20% polymer was 74 mS/cm.

Example 4

Formation of Gel with Polyacrylic Acid

Example 2 was repeated with polyacrylic acid as the polymer. The results were the same. The gel conductivity at 23% polymer was 76 mS/cm.

Example 5

Formation of α-Picoline Salt with Hydrogen Fluoride

About 60 grams of anhydrous hydrogen fluoride was added slowly to about 69 grams of α-picoline contained in an autoclave with stirring, giving a picoline to HF mole ratio of 1:3. When the heat of the reaction subsided and the mixture cooled down, the autoclave contained 129 grams of a liquid, boiling at 200° C., 80° C. higher than that of α-picoline and 180° C. higher than that of hydrogen fluoride. The liquid could not be separated into the constituents. The analysis of the material confirmed the structure of the new compound as the ionic liquid [α-picoline·H$^+$] [H$_2$F$_3$]$^-$ (or α-picoline·3HF). The conductivity of the pure ionic liquid was measured as 73 mS/cm. The liquid did not etch borosilicate glass, unlike Olah's reagent, which reacts with glass.

The foregoing examples illustrate a wide variety of compounds according to the present invention that may be prepared having utility in a wide variety of solvent applications, and as non-aqueous electrolytes for various electrochemical devices. It will be apparent to one of skill in the art based on the properties apparent from the foregoing examples that a wide range of other applications are possible with the compounds according to the invention, and that the invention includes a wide range of compounds that are not specifically demonstrated by the examples, but that may be obtained by application of the principles demonstrated.

What is claimed is:

1. A polymeric ionic gel comprising:
A non-aqueous ionic liquid having a melting point less than about 100° C., the ionic liquid comprising the reaction product of a reaction of at least one heterocyclic amine with between 2.8 and 3.2 moles of anhydrous hydrogen fluoride per mole of amine nitrogen; and
an amount of a polyacrylic acid effective to form a gel of said non-aqueous ionic liquid;
wherein said heterocyclic amine is selected from the group consisting of substituted and unsubstituted pyrroles, substituted and unsubstituted pyrazoles, substituted and unsubstituted pyridines, substituted and unsubstituted pyrazines, substituted and unsubstituted pyrimidines, substituted and unsubstituted pyridazines, substituted and unsubstituted thiazoles, substituted and unsubstituted oxyazoles, substituted and unsubstituted triazoles, substituted and unsubstituted pyrrolidines, substituted and unsubstituted pyrrolidones, substituted and unsubstituted piperazines, substituted and unsubstituted piperidines, substituted and unsubstituted pyrrolines, and a multi-cyclic fused ring structure containing from 8 to 14 ring members, with from 1 to 3 ring members being a heteroatom selected from the group consisting of nitrogen, oxygen and sulfur, wherein at least one of said heteroatoms is nitrogen.

2. A polymeric ionic gel according to claim 1, wherein said ionic liquid consists of one heterocyclic amine ionic compound.

3. A polymeric ionic gel according to claim 1, wherein said ionic liquid consists of two or more heterocyclic amine compounds.

4. The polymeric ionic gel of claim 1, having a specific conductivity between one and 600 milli-siemens/cm.

5. The polymeric ionic gel of claim 1, wherein said heterocyclic amine is pyridine or a picoline.

6. The polymeric ionic gel of claim 1, wherein said heterocyclic amine is selected from the group consisting of substituted and unsubstituted quinolines, substituted and unsubstituted quinoxilines, substituted and unsubstituted purines and substituted and unsubstituted isoquinolines.

7. The polymeric ionic gel of claim 1, comprising between 2 and 50% by weight of polymer.

8. The polymeric ionic gel of claim 1, wherein said polyacrylic acid is a Group I metal salt of a polyacrylic acid.

9. The polymeric ionic gel of claim 1, wherein said polyacrylic acid comprises an acrylic acid or Group I metal salt thereof copolymerized with one or more vinyl co-monomers selected from the group consisting of acrylic acid-alkyl esters, alkyl-branched acrylic acids, alkyl-branched acrylic acid alkyl esters, alkyl-branched acrylic acid Group I metal salts, vinyl halides, vinyl acetate, vinyl alcohol, vinyl ethers, maleic anhydride, acrylonitrile and styrene.

10. The polymeric ionic gel of claim 1, wherein the ionic liquid has a melting point less than 60° C.

* * * * *